(12) United States Patent
Shi et al.

(10) Patent No.: US 12,636,425 B2
(45) Date of Patent: May 26, 2026

(54) REMOTE-CONTROL DEFECATION DEVICE FOR DISABLED CONSTIPATION PATIENTS

(71) Applicant: Huzhou College, Huzhou City (CN)

(72) Inventors: Ying Shi, Huzhou City (CN); Yanqiong Zhang, Huzhou City (CN); Donghui Wan, Huzhou City (CN)

(73) Assignee: Huzhou College, Huzhou City (CN)

( * ) Notice: Subject to any disclaimer, the term of this patent is extended or adjusted under 35 U.S.C. 154(b) by 483 days.

(21) Appl. No.: 18/486,591

(22) Filed: Oct. 13, 2023

(65) Prior Publication Data

US 2025/0041505 A1 Feb. 6, 2025

(30) Foreign Application Priority Data

Aug. 2, 2023 (CN) .......................... 202310965255.0

(51) Int. Cl.
| | |
|---|---|
| *A61M 3/02* | (2006.01) |
| *A61B 8/12* | (2006.01) |
| *A61M 1/00* | (2006.01) |
| *A61M 39/22* | (2006.01) |
| *A61M 25/00* | (2006.01) |

(52) U.S. Cl.
CPC ............. *A61M 3/0283* (2013.01); *A61B 8/12* (2013.01); *A61M 1/77* (2021.05); *A61M 1/80* (2021.05); *A61M 3/02* (2013.01); *A61M 3/0202* (2021.05); *A61M 3/0233* (2013.01); *A61M 3/0254* (2013.01); *A61M 39/22* (2013.01); *A61M 2025/0004* (2013.01); *A61M 2205/3375* (2013.01); *A61M 2205/3576* (2013.01); *A61M 2210/1067* (2013.01)

(58) Field of Classification Search
CPC .... A61M 3/0283; A61M 3/02; A61M 3/0202; A61M 3/0233; A61M 3/0254; A61M 1/77; A61M 1/80; A61B 8/12
See application file for complete search history.

(56) References Cited

U.S. PATENT DOCUMENTS

| | | | | |
|---|---|---|---|---|
| 694,541 | A | * | 3/1902 | Gordon ............... A61M 3/0283 604/39 |
| 2006/0173244 | A1 | * | 8/2006 | Boulais .................. A61B 1/015 600/156 |

FOREIGN PATENT DOCUMENTS

| | | | | |
|---|---|---|---|---|
| CN | 117703818 A | * | 3/2024 | ............. F04D 13/16 |

* cited by examiner

*Primary Examiner* — Tasnim Mehjabin Ahmed
(74) *Attorney, Agent, or Firm* — COOPER LEGAL GROUP LLC

(57) ABSTRACT

Remote-control defecation device for disabled constipation patients includes a supply and discharge pipe including a supply and discharge outer pipe and a supply and discharge inner pipe; a sewage discharge pump communicated with a sewage discharge space; an ultrasonic detector at one end of the supply and discharge inner pipe; electric opening-closing doors arranged on the supply and discharge outer pipe in a circumferential direction; electric rotating blades arranged on the supply and discharge inner pipe in a circumferential direction and located in the sewage discharge space between the supply and discharge outer pipe and the supply and discharge inner pipe; and a water supply pipe arranged inside of the supply and discharge outer pipe, with one end of the water supply pipe provided with a water supply valve communicated with the outside, and the other end of the water supply pipe communicated with a water supply pump.

8 Claims, 3 Drawing Sheets

REMOTE-CONTROL DEFECATION DEVICE FOR DISABLED CONSTIPATION PATIENTS

CROSS-REFERENCE TO RELATED APPLICATIONS

This application claims priority to Chinese Patent Application No. 202310965255.0, filed on Aug. 2, 2023, the entire contents of which are incorporated herein by reference.

TECHNICAL FIELD

The application belongs to the technical field of medical nursing equipment, and in particular to a remote-control defecation device for disabled constipation patients.

BACKGROUND

Nowadays, aging is becoming increasingly serious, and many elderly people or patients who have chronic bedrest are prone to constipation because of factors such as less exercise and illness. Severe constipation will lead to abdominal distension and difficulty in defecation, which will cause certain harm to the body.

At present, there is a lack of nursing equipment for patients who can't defecate autonomously. The defecation of patients mainly needs manual operations such as hand and bowel cleaning, which has high labor intensity, bad working environment and poor patient comfort. The defecation problem of patients who can't defecate autonomously, especially the elderly disabled patients, has not been properly solved so far.

SUMMARY

In order to solve the above technical problems, the application provides a remote-control defecation device for disabled constipation patients, aiming at solving or improving at least one of the above technical problems.

In order to achieve the above objective, the present application provides a remote-control defecation device for disabled constipation patients, including:

a supply and discharge pipe, where the supply and discharge pipe includes a supply and discharge outer pipe and a supply and discharge inner pipe arranged inside the supply and discharge outer pipe, one end of the supply and discharge inner pipe is connected with one end of the supply and discharge outer pipe, and a sewage discharge space is formed between the supply and discharge outer pipe and the supply and discharge inner pipe;

a sewage discharge pump communicated with the sewage discharge space;

an ultrasonic detector arranged at the end of the supply and discharge inner pipe, where a detection end of the ultrasonic detector penetrates through the supply and discharge outer pipe;

a plurality of electric opening-closing doors arranged on the supply and discharge outer pipe in a circumferential direction;

a plurality of electric rotating blades, where the electric rotating blades are arranged on the supply and discharge inner pipe in a circumferential direction and the electric rotating blades are located in the sewage discharge space;

a water supply pipe, where the water supply pipe is arranged inside of the supply and discharge outer pipe, one end of the water supply pipe, adjacent to the ultrasonic detector, is provided with a water supply valve, and the other end of the water supply pipe is communicated with a water supply pump, and the water supply valve is communicated with the outside.

Optionally, the remote-control defecation device for disabled constipation patients also includes a controller, and the ultrasonic detector, the sewage discharge pump, the water supply valve, the water supply pump, the electric opening-closing doors and the electric rotating blades are all electrically connected with the controller.

Optionally, a space formed by the plurality of electric opening-closing doors and the supply and discharge inner pipe forms a sewage crushing cavity, and the electric rotating blades are located in the sewage crushing cavity.

Optionally, the remote-control defecation device for disabled constipation patients also includes a pipe wheel bracket, where a pipe storage wheel is installed on the pipe wheel bracket, and the supply and discharge pipe is wound on the pipe storage wheel.

Optionally, the supply and discharge inner pipe is made of nylon.

Optionally, the supply and discharge outer pipe is made of plastic.

Optionally, the sewage discharge pump is a powerful direct-current sewage discharge pump.

Optionally, the water supply pump is a variable-speed direct-current pump.

Compared with the prior art, the application has the following advantages and technical effects.

The ultrasonic detector is used to detect the status of feces in rectum and colon, and the water supply pump, the water supply valve, the sewage discharge pump, the electric opening-closing doors and the electric rotating blades are controlled to be turned on, so that water flows out through the water supply pipe and the water supply valve to achieve the effect of flushing out human feces, the feces enter the sewage discharge space through the electric opening-closing doors, the feces are cracked by the electric rotating blades, and the cracked feces are forcefully discharged from the sewage discharge space between the supply and discharge outer pipe and the supply and discharge inner pipe by the sewage discharge pump. The remote-control defecation device for disabled constipation patients is easy to operate, highly applicable, convenient to use, and is especially suitable for patients who have long-term constipation and are disabled and unable to defecate spontaneously, which is helpful to relieve the pain of patients, improve the working environment of nursing staff and reduce the labor intensity.

BRIEF DESCRIPTION OF THE DRAWINGS

The accompanying drawings, which constitute a part of this application, are used to provide a further understanding of this application. The illustrative embodiments of this application and their descriptions are used to explain this application, and do not constitute an improper limitation of this application.

DETAILED DESCRIPTION OF THE EMBODIMENTS

In the following, the technical scheme in the embodiment of the application will be clearly and completely described with reference to the attached drawings. Obviously, the described embodiment is only a part of the embodiment of the application, but not the whole embodiment. Based on the embodiments in the present application, all other embodiments obtained by ordinary technicians in the field without creative labor belong to the scope of protection of the present application.

In order to make the above objectives, features and advantages of the present application more obvious and easier to understand, the present application will be further described in detail with the attached drawings and specific embodiments.

Figure 1:
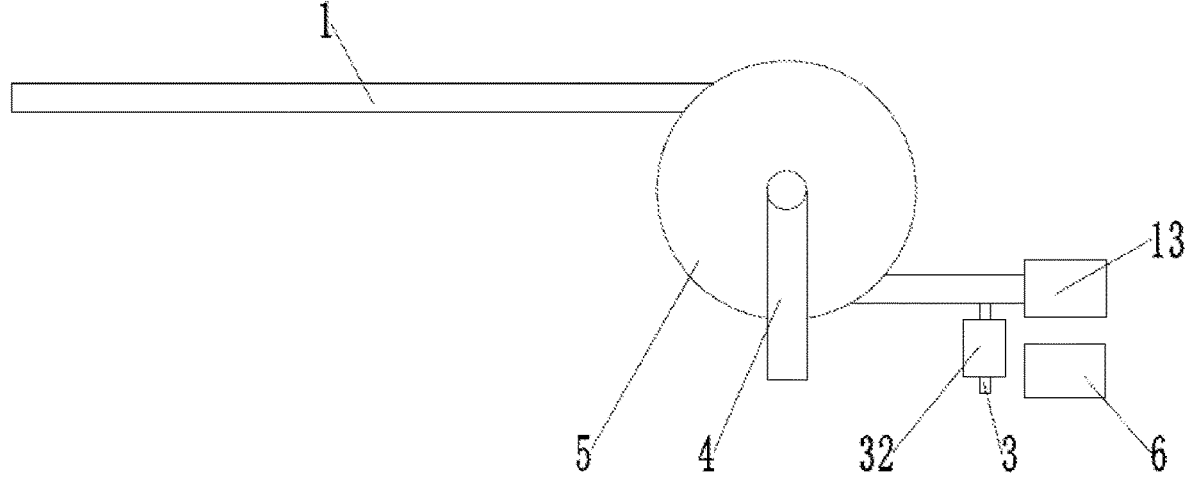
FIG. 1 is a schematic diagram of an overall structure of the present application.
Figure 2:
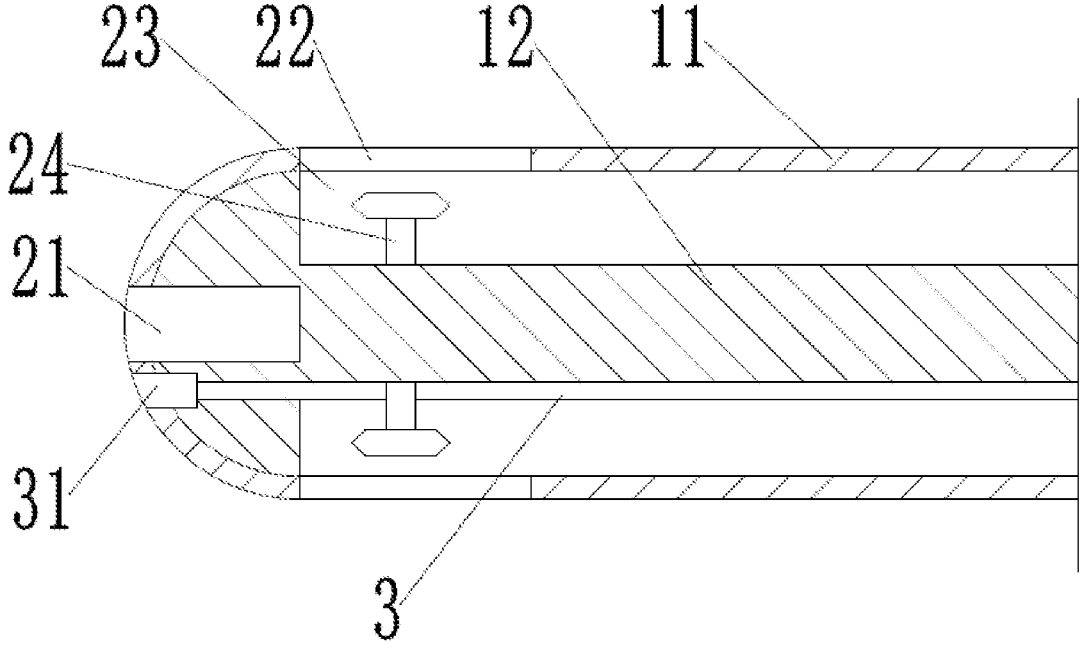
FIG. 2 is a schematic structural diagram of ends of a supply and discharge pipe in the present application.
Figure 3:
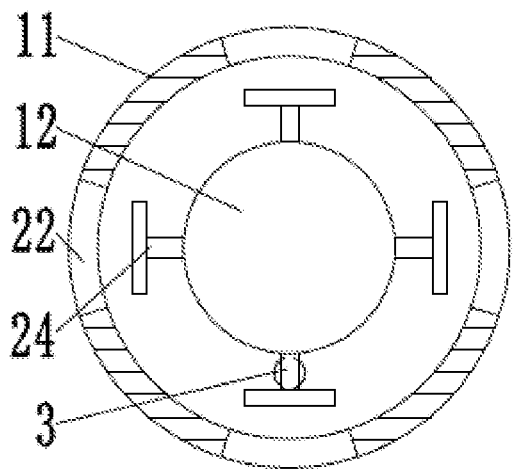
FIG. 3 is a side view of ends of a supply and discharge pipe in the present application.

Referring to FIG. 1-FIG. 3, this embodiment provides a remote-control defecation device for disabled constipation patients, including:

a supply and discharge pipe 1, where the supply and discharge pipe 1 includes a supply and discharge outer pipe 11 and a supply and discharge inner pipe 12 arranged inside the supply and discharge outer pipe 11, one end of the supply and discharge inner pipe 12 is connected with one end of the supply and discharge outer pipe 11, and a sewage discharge space is formed between the supply and discharge outer pipe 11 and the supply and discharge inner pipe 12;

a sewage discharge pump 13 communicated with the sewage discharge space;

an ultrasonic detector 21 arranged at the end of the supply and discharge inner pipe 12 12, where the detection end of the ultrasonic detector 21 penetrates through the supply and discharge outer pipe 11;

a plurality of electric opening-closing doors 22 arranged on the supply and discharge outer pipe 11 in the circumferential direction;

a plurality of electric rotating blades 24, where the electric rotating blades 24 are arranged on the supply and discharge inner pipe 12 in the circumferential direction and the electric rotating blades 24 are located in the sewage discharge space;

a water supply pipe 3, where the water supply pipe 3 is arranged inside the supply and discharge outer pipe 11, one end of the water supply pipe 3, adjacent to the ultrasonic detector 21, is provided with a water supply valve 31, the other end of the water supply pipe 3 is a water supply pump 32, and the water supply valve 31 is communicated with the outside.

The ultrasonic detector 21 is used to detect the status of feces in rectum and colon, and the water supply pump 32, the water supply valve 31, the sewage discharge pump 13, the electric opening-closing doors 22 and the electric rotating blades 24 are controlled to be turned on, so that the water flows out through the water supply pipe 3 and water supply valve 31, so as to achieve the function of flushing out human feces. The feces enter the sewage discharge space through the electric opening-closing doors 22, and are cracked by the electric rotating blades 24, and the cracked feces are forcefully discharged from the sewage discharge space between the supply and discharge outer pipe 11 and the supply and discharge inner pipe by the sewage discharge pump 13.

In an embodiment, the remote-control defecation device for disabled constipation patients also includes a controller 6, and the ultrasonic detector 21, the sewage discharge pump 13, the water supply valve 31, the water supply pump 32, the electric opening-closing doors 22 and the electric rotating blades 24 are all electrically connected with the controller 6.

The controller 6 receives the signal fed back by the ultrasonic detector 21, and simultaneously control the sewage discharge pump 13, the water supply valve 31, the water supply pump 32, the electric opening-closing doors 22 and the electric rotating blades 24 to be turned on. The controller 6 is a single-chip system microcontroller with a built-in memory, a central processing unit, an interface circuit, wireless communication and a Bluetooth module, and is capable of receiving various detection signals, data information and instructions, sending out control operation commands, coordinating control operations and realizing remote-control control and telemetry functions. It is capable of accepting the instructions from the control handle, communicating wirelessly with the monitoring center, and exchanging instructions and data. Through the monitoring center, the controller is capable of being connected to the mobile communication network and the Internet of Things, and sending relevant information to the mobile phone or the Internet of Things cloud center.

The electric opening-closing doors 22 are miniature electric-control guide rail sealed sliding doors, which are closed at ordinary times and opened at work.

The electric rotating blades 24 are miniature electric rotating blades which are strongly waterproof and controlled.

In an embodiment, a space formed by the plurality of electric opening-closing doors 22 and the supply and discharge inner pipe 12 forms a sewage crushing cavity 23, and the electric rotating blades 24 are located in the sewage crushing cavity 23.

By controlling the opening of the electric opening-closing doors 22 and the rotation speed of the electric rotating blades 24, the faeces enter the sewage crushing cavity 23 under the negative pressure generated by the sewage discharge pump 13, so that the faeces are agglomerated and crushed by the rotation of the electric rotating blades 24, and the faeces are easily discharged from the sewage discharge space.

The supply and discharge inner pipe and the supply and discharge outer pipe are preferably fixedly connected at the end of the head assembly to facilitate the stability of the angle adjustment of the head assembly 2.

In an embodiment, the remote-control defecation device for disabled constipation patients also includes a pipe wheel bracket 4. A pipe storage wheel 5 is installed pipe wheel bracket 4, and the supply and discharge pipe 1 is wound on the pipe storage wheel 5.

The pipe wheel bracket 4 is used to support the pipe storage wheel 5. The pipe storage wheel 5 is used for accommodating the supply and discharge pipe 1.

In an embodiment, the supply and discharge inner pipe 12 is made of nylon which is high in strength and high in elasticity and nontoxic, and the supply and discharge inner pipe 12 is preferably a medical endoscope with an ultrasonic detector 21 at the head and steering function. The steering function is controlled by the controller 6. The steering function is the prior art, so it will not be repeated here.

In an embodiment, the supply and discharge outer pipe 11 is made of plastic, which is high in strength, high in elasticity, high in toughness and non-toxic.

In an embodiment, the sewage discharge pump 13 is a powerful direct-current sewage discharge pump.

The discharge force of the sewage discharge pump 13 is adjusted by the controller 6, and the outlet of the sewage discharge pump 13 is connected to a sewer or a collection container.

In an embodiment, the water supply pump 32 is a variable-speed direct-current pump.

The controller 6 is capable of adjusting the water flow injected by the water supply pump 32.

A Method for Using the Emote Defecation Device for Disabled Constipation Patients > S1, connecting the remote-control defecation device for disabled constipation patients to the power supply, receiving, by the controller 6, the instructions and various operating parameters sent from the monitoring center, and controlling the device to operate by the controller 6 according to the instructions of the monitoring center or the control handle;
>
> S2, inserting the head of the discharge pipe 1 by the professional into the patient's body, and sending out relevant instructions by the ultrasonic detector 21 according to the detected images of the rectum or colon;
>
> S3, receiving relevant instructions by the controller 6 to control the water supply pump 32 to start, the water supply valve 31 to open to spray water to a designated part when stool accumulated in the patient needs to be discharged; starting the sewage discharge pump 13, opening the electric opening-closing doors 22, and rotating the electric rotating blades 24 to crack and discharge faeces; and
>
> S4, after the operation, cleaning and disinfecting the remote-control defecation device for disabled constipation patients for the next use.

During operation, the controller 6 performs data communication with the monitoring center in real time, and exchanges data with related mobile devices and medical Internet of Things through the monitoring center.

In the description of the present application, it should be noted that the orientation or position relationships indicated by the terms "longitudinal", "transverse", "upper", "lower", "front", "rear", "left", "right", "vertical", "horizontal", "top", "bottom", "inner", "outer" are based on the orientation or position relationships shown in the figures, which are only for the convenience of describing the present application, rather than indicating or implying that the device or elements must be in designated orientation, or configured or operated in designated orientation so that they cannot be understood as the limitation of this application.

The above-mentioned embodiments only describe the preferred mode of the present application, and do not limit the scope of the present application. Without departing from the design spirit of the present application, all kinds of modifications and improvements made by ordinary technicians in the field to the technical scheme of the present application should fall within the protection scope determined by the claims of the present application.

What is claimed is:

1. A remote-control defecation device for disabled constipation patients, comprising:

a supply and discharge pipe, wherein the supply and discharge pipe comprises a supply and discharge outer pipe and a supply and discharge inner pipe arranged inside the supply and discharge outer pipe, one end of the supply and discharge inner pipe is connected with one end of the supply and discharge outer pipe, and a sewage discharge space is formed between the supply and discharge outer pipe and the supply and discharge inner pipe;

a sewage discharge pump communicated with the sewage discharge space;

an ultrasonic detector arranged at the end of the supply and discharge inner pipe, wherein a detection end of the ultrasonic detector penetrates through the supply and discharge outer pipe;

a plurality of electric opening-closing doors arranged on the supply and discharge outer pipe in a circumferential direction;

a plurality of electric rotating blades, wherein the electric rotating blades are arranged on the supply and discharge inner pipe in a circumferential direction and the electric rotating blades are located in the sewage discharge space; and a water supply pipe, wherein the water supply pipe is arranged inside of the supply and discharge outer pipe, one end of the water supply pipe, adjacent to the ultrasonic detector, is provided with a water supply valve, and an other end of the water supply pipe is communicated with a water supply pump, and the water supply valve is communicated with an outside.

2. The remote-control defecation device for disabled constipation patients according to claim 1, further comprising a controller, wherein the ultrasonic detector, the sewage discharge pump, the water supply valve, the water supply pump, the electric opening-closing doors and the electric rotating blades are all electrically connected with the controller.

3. The remote-control defecation device for disabled constipation patients according to claim 1, wherein a space formed by the plurality of electric opening-closing doors and the supply and discharge inner pipe forms a sewage crushing cavity, and the electric rotating blades are located in the sewage crushing cavity.

4. The remote-control defecation device for disabled constipation patients according to claim 1, further comprising a pipe wheel bracket, wherein a pipe storage wheel is installed on the pipe wheel bracket, and the supply and discharge pipe is wound on the pipe storage wheel.

5. The remote-control defecation device for disabled constipation patients according to claim 1, wherein the supply and discharge inner pipe is made of nylon.

6. The remote-control defecation device for disabled constipation patients according to claim 1, wherein the supply and discharge outer pipe is made of plastic.

7. The remote-control defecation device for disabled constipation patients according to claim 1, wherein the sewage discharge pump is a powerful direct-current sewage discharge pump.

8. The remote-control defecation device for disabled constipation patients according to claim 1, wherein the water supply pump is a variable-speed direct-current pump.

* * * * *